United States Patent [19]
vanHooydonk

[11] Patent Number: 5,902,251
[45] Date of Patent: May 11, 1999

[54] TRANSCERVICAL INTRAUTERINE APPLICATOR FOR INTRAUTERINE HYPERTHERMIA

[76] Inventor: Neil C. vanHooydonk, 2310 Aspen St., Richardson, Tex. 75082

[21] Appl. No.: 08/851,099

[22] Filed: May 5, 1997

Related U.S. Application Data

[60] Provisional application No. 60/016,898, May 6, 1996.
[51] Int. Cl.$^6$ .................................................. A61B 10/00
[52] U.S. Cl. .............................. 600/549; 606/28; 606/33
[58] Field of Search .............................. 600/549; 606/33, 606/28; 128/1, 2, 3

[56] References Cited

U.S. PATENT DOCUMENTS

| | | | |
|---|---|---|---|
| 2,407,690 | 9/1946 | Southworth | 128/422 |
| 3,369,549 | 2/1968 | Armao | 606/28 |
| 4,154,246 | 5/1979 | LeVeen | 128/784 |
| 4,311,154 | 1/1982 | Sterzer et al. | 128/804 |
| 4,583,556 | 4/1986 | Hines et al. | 128/804 |
| 4,601,296 | 7/1986 | Yerushalmi | 128/804 |
| 4,658,836 | 4/1987 | Turner | 128/804 |
| 4,700,716 | 10/1987 | Kasevich et al. | 128/804 |
| 4,813,429 | 3/1989 | Eshel et al. | 128/736 |
| 4,825,880 | 5/1989 | Stauffer et al. | 128/804 |
| 4,841,988 | 6/1989 | Fetter et al. | 128/804 |
| 4,967,765 | 11/1990 | Turner et al. | 128/785 |
| 4,979,948 | 12/1990 | Geddes et al. | 606/33 |
| 5,007,437 | 4/1991 | Sterzer | 428/786 |
| 5,057,106 | 10/1991 | Kasevich et al. | 606/33 |
| 5,226,430 | 7/1993 | Spears et al. | 600/28 |
| 5,443,470 | 8/1995 | Stern et al. | 607/98 |
| 5,480,417 | 1/1996 | Hascoet et al. | 607/101 |
| 5,549,559 | 8/1996 | Esnel | 606/28 |

FOREIGN PATENT DOCUMENTS

| | | |
|---|---|---|
| 0105677 | 4/1984 | European Pat. Off. . |
| 0248758 | 12/1987 | European Pat. Off. . |
| 0370890 | 5/1996 | European Pat. Off. . |
| 2679456 | 1/1993 | France .............................. A61N 5/02 |

OTHER PUBLICATIONS

Asherman, "Amenorrhoea Traumatica (Atretica)," Department of Obstetrics and Gynaecology, Hadassah Municipal Hospital, Tele–Aviv, Palestine, pp. 23–30, 1947.

Asherman, "Traumatic Intra–Uterine Adhesions," Department of Obstetrics and Gynaecology, Hasassa Municipal Hospital, Tel–Aviv, Israel, pp. 892–896, Jun., 1950.

Siroky, et al, "The Flow Rate Nomogram: I. Development," Department of Urology, Boston University Medical Center, Boston, Massachusetts, pp. 665–668, Jan. 5, 1979.

Siroky, et al, "The Flow Rate of Nomogram: II. Clinical Correlation," Department of Urology, Boston University Medical Center, Boston, Massachusetts, pp. 208–210, Apr. 6, 1979.

Mendecki, et al, "Microwave Applicators for Localized Hyperthermia Treatment of Cancer of the Prostate," Int. J. Radiation Oncology Biol. Phys., vol. 6, pp. 1583–1588, 1980.

Yerushalmi, et al, "Normal Tissue Response to Localized Deep Microwave Hyperthermia in the Rabbit's Prostate: A Preclinical Study," Int. J. Radiation Oncology Biol. Phys., vol. 9, pp. 77–82, 1982.

(List continued on next page.)

*Primary Examiner*— Max Hindenburg
*Assistant Examiner*—Pamela L. Wingood
*Attorney, Agent, or Firm*—Sidley & Austin

[57] ABSTRACT

A transcervical intrauterine catheter applicator for the hyperthermia/thermal therapy treatment of the uterus. The applicator includes one or more EMR antennas and one or more temperature sensors for measuring the temperature of the endometrial tissue. Each EMR antenna has an elongated helical coil connected to the center conductor of a coaxial cable to thereby generate a light bulb shaped radiation pattern and thus generate a similar-shaped pattern of thermal energy in the endometrium tissue. The catheter can be of the balloon type that can be inflated, thereby radially moving the antenna and temperature sensor against the walls of the uterus.

22 Claims, 11 Drawing Sheets

OTHER PUBLICATIONS

Dicker, et al, "Complications of Abdominal and Vaginal Hysterectomy Among Women of Reproductive Age in the United States—The Collaborative Review of Sterilization," Am. J. Obstet. Gynecol., pp., 841–8 48, Dec. 1, 1982.

Harada, et al, "Microwave Surgical Treatment of Diseases of Prostate," Urology, pp. 572–576, Dec., 1985.

Matsuda, et al, "Heat Application for Clinical Carcinoma of the Esophagus," Proceedings of the 5th International Symposium on Hyperthermic Oncology, Kyoto, Japan, Aug. 29–Sep. 3, 1988.

McGuire, "Transurethral Hyperthermia for BPH: Trial Goal is to Top 80% Success," Medical Tribune, vol. 29, No. 9, Mar. 31, 1988.

Sapozink, et al, "Transurethral Hyperthermia for Benign Prostatic Hyperplasia: Preliminary Clinical Results," The Journal of Urology, vol. 143, pp. 944–950, May, 1990.

Phipps, et al, "Experimental and Clinical Studies with Radiofrequency–Induced Thermal Endometrial Ablation for Functional Menorrhagia," Obstetrics & Gynecology, vol. 76, No. 5, Part 1, pp. 876–881, Nov., 1990.

Wortman, et al, "Hysteroscopic Management of Intractable Uterine Bleeding—A Review of 103 Cases", Journal of Reproductive Medicine, vol. 38, No. 7, pp. 505–510, Jul., 1993.

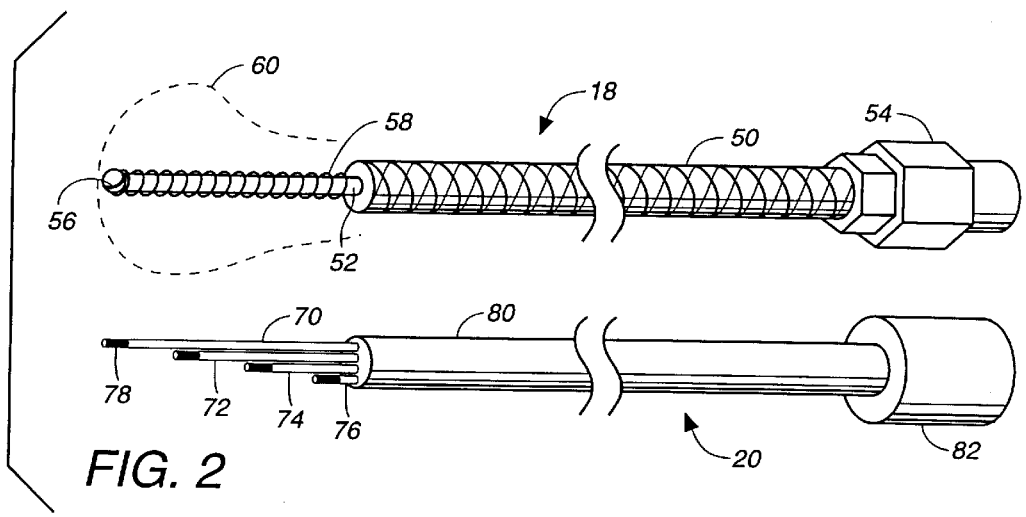
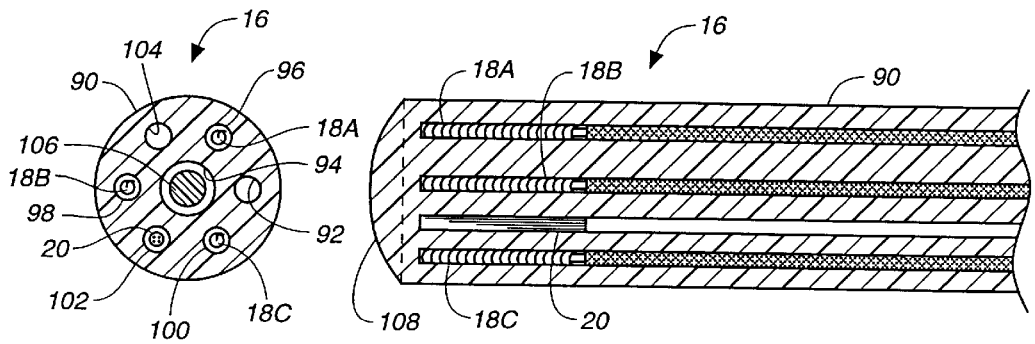
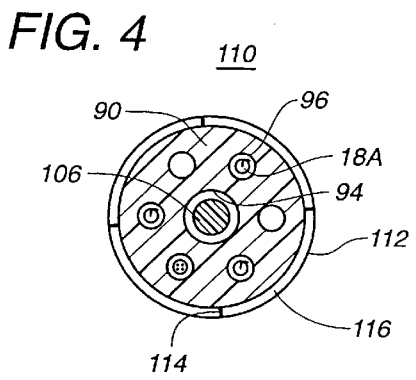
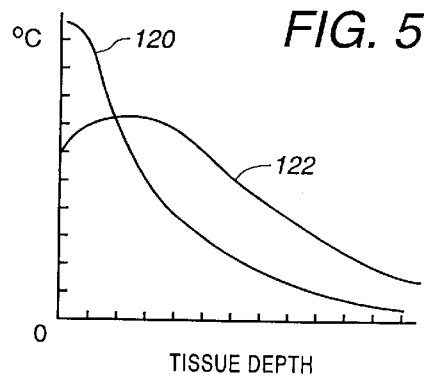

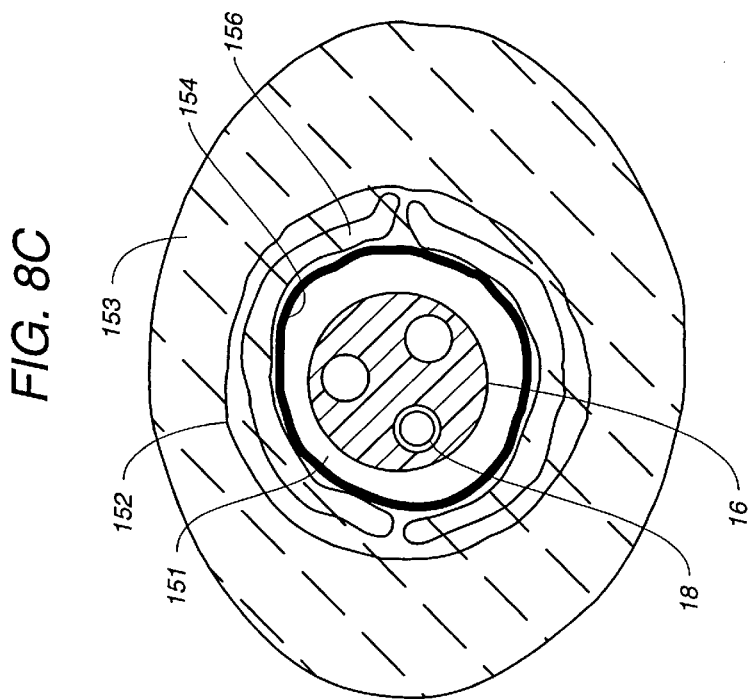
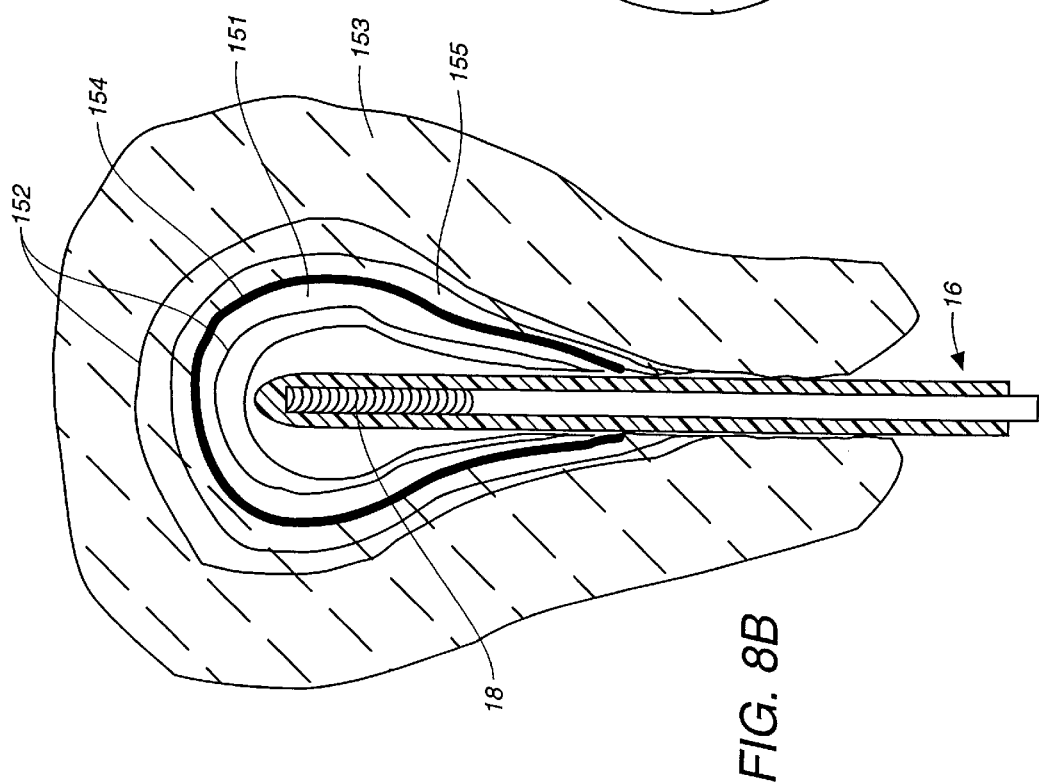

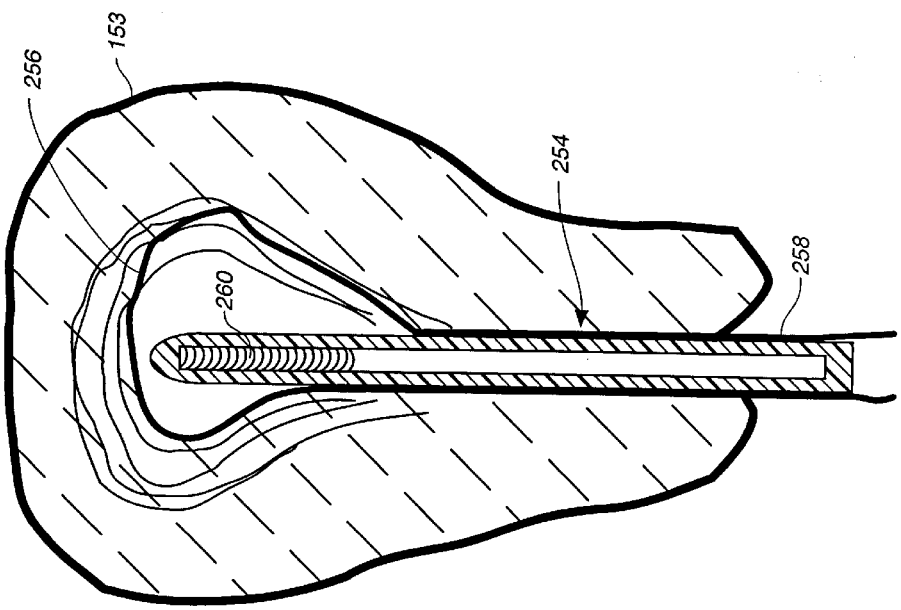
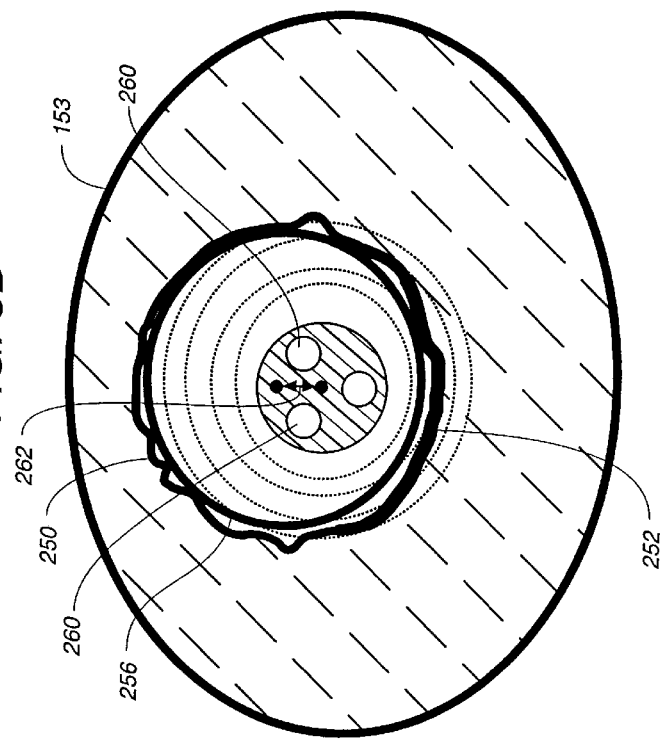

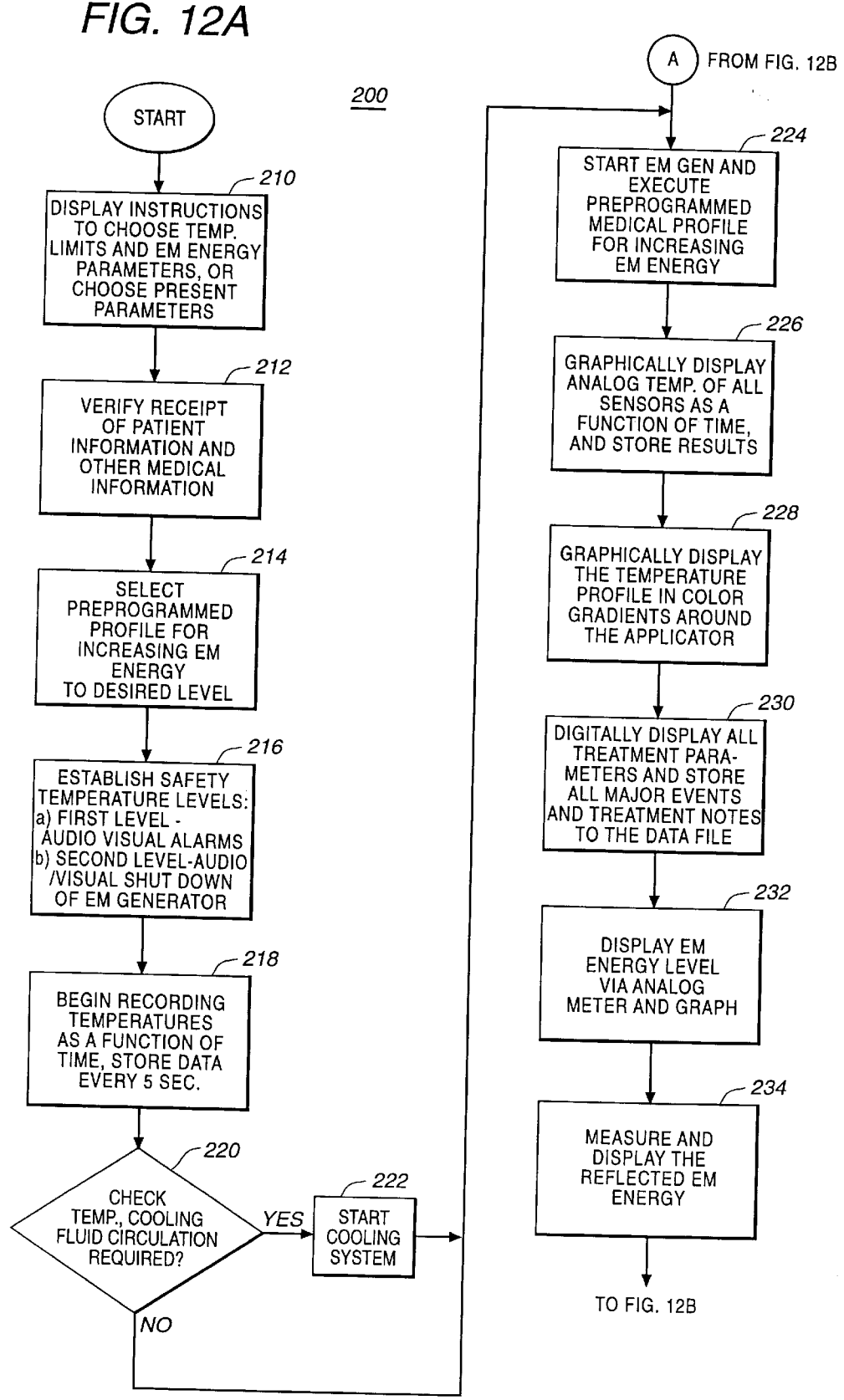

TRANSCERVICAL INTRAUTERINE APPLICATOR FOR INTRAUTERINE HYPERTHERMIA

RELATED APPLICATION

This application claims of the benefit of prior filed U.S. Provisional Application No. 60/016,898 filed Apr. 6, 1996.

TECHNICAL FIELD OF THE INVENTION

This invention relates to an electromagnetic radiation (EMR) device for the medical treatment by above-normal temperatures of dysfunctional (abnormal) uterine bleeding whose major symptom is menorrhagia (excessively profuse or prolonged menstruation).

BACKGROUND OF THE INVENTION

Hyperthermia (i.e., thermal therapy or intentionally induced above normal temperature, has proved to be beneficial in treating tumors (both benign and malignant growths) in animals and humans. External wave guide applicators have been used to treat superficial lesions; wave guide applicators positioned around a body or limb have been used in an attempt to heat deep seated lesions; interstitial (within the tissue) antennas have been employed to invasively treat tumors such as unresectable breast cancer; and intracavitary (inside a naturally occurring cavity, a.k.a. intraluminal, endotract, etc.) approaches have been employed to heat growths in, and adjacent to, naturally occurring cavities such as the esophagus and the prostatic urethra.

Attempts to employ EMR to heat subsurface growths ordinarily result in temperatures in the intervening normal or non-targeted tissue reaching hazardous levels before the tumor or target tissue temperatures reach prescribed thermal dose levels. The advantage of interstitial and intracavitary approaches is that the applicator is positioned inside or adjacent to the target tissue. Thus, heating is localized to the area immediately around the source of the EMR, is confined to the target tissue, and does not overheat significant amounts of non-targeted tissue before reaching the desired temperature in the target tissue.

The major advantage of an intracavitary approaches is that it is minimally invasive (unlike interstitial techniques), non-surgical, and allows direct access to the target tissue.

The terms hyperthermia and thermal therapy are used herein interchangeably. Hyperthermia is broadly defined herein as any above normal temperature and includes terms of fever (37–41.5 degree C), hyperthermia (typically defined as 41.5–45 degree C), thermal therapy (typically defined as 45–55 degree C), coagulation necrosis (>55 degree C), cauterization, etc.

U.S. Pat. No. 2,407,690 by Southworth teaches the advantages of using external wave guide apparatus for diathermy and how the wave can be directed down tubular orifices. But the Southworth body passage insertable waveguide applicator concentrates the heating pattern at the radiating tip of the applicator. Thus, the use of Southworth type applicator results in non-uniform heating of the tissues along the length of a tubular organ.

U.S. Pat. No. 4,154,246 by LeVeen describes an RF helical antenna with the helical antenna coils wound tightly together (i.e., windings without any space therebetween) for interstitial and intracavitary use. The LeVeen helical coil antenna propagates energy from the distal tip of the applicator.

U.S. Pat. No. 4,658,836 by Turner is stated to be for a microwave antenna that provides uniform heating along the length of the esophagus.

U.S. Pat. No. 4,700,716 by Kasevich et al discloses a device that provides uniform heating along the entire length of the applicator array.

Dipole type antennas have been employed in intracavitary applicators, but such type of applicators concentrate the energy propagation and result in a heating pattern around the "junction" that is proximal to the distal tip of the antenna.

U.S. Pat. No. 4,825,880 by Stauffer et al., illustrates an implantable helical coil antenna adaptable for interstitial hyperthermia that is designed with a "gap" between the proximal end of the coil and the outer coaxial conductor. This design provides uniform heat along the active length of the coil and the heating pattern is unaffected by the insertion depth.

U.S. Pat. No. 4,583,566 by Hines describes a helical antenna that is substantially equivalent to the Stauffer et al., design except that there is no "gap", in that the proximal end of the antenna coil is connected to the outer conductor. In the Haines patent, it is contended that the design provides more uniform heating along the length of the coil.

U.S. Pat. Nos. 5,097,845 and 4,841,988 by Fetter et al., describe a helical coil antenna that is similar to the Hines design, except that the separation between the windings varies in an attempt to provide uniform heating along the axial length of the antenna.

Intracavitary hyperthermia has been employed to treat cancer of the prostate (CaP), benign prostatic hypertrophy (BPH), and other conditions of the prostate. Both atransrectal and transurethral treatment approaches have been developed.

Mendecki et al., described in a publication entitled "Microwave Applicators for Localized Hyperthermia Treatment of Cancer of the Prostate"; *Int. J. Radiation Oncology, Bio., Phys.*, Vol. 6, pp 1583–1588), 1978, a transrectal applicator with a dipole antenna for the treatment of CaP.

U.S. Pat. No. 4,311,154 by Sterzer et al., describes a transrectal applicator (identical to that described by Mendecki, et al) that is equipped with a temperature sensor in a transurethral catheter to monitor temperatures.

Yerushalmi et al., published an article "Normal Tissue Response to Localized Deep Microwave Hyperthermia in the Rabbit's Prostate: A Preclinical Study"; *Int. J. Radiation Oncology, Bio., Phys.*, Vol. 9, pp 77–82, 1982, describing the results of transrectal hyperthermia experiments on rabbit tissue. U.S. Pat. No. 4,601,296 by Yerushalmi describes a transrectal applicator with channels for circulating a cooling agent around the surface of the applicator to spear the rectal wall tissues in contact with the applicator. Subsequently, a number of publications and patents have been issued for different designs for transrectal applicators (e.g., Eshel, European patent application 0 248 758 A1; and Eshel et al., U.S. Pat. No. 4,813,429).

Transurethral hyperthermia has been employed to principally treat benign prostatic hyperplasia (BPH). Mebust reports in the editorial comments section of another publication entitled "Transurethral Hyperthermia for Benign Prostatic Hyperplasia; Preliminary Clinical Results"; *The Journal of Urology;* Vol. 143, May, 1977, that in 1977 a high frequency electrical surgical current was used in a transurethral approach to treat patients with BPH.

As described in the article entitled, "Microwave Surgical Treatment of Diseases of Prostate"; *Urology, Vol.* XXVL, Number 6; pp 572–576, 1985, Harada et al., employed transurethral hyperthermia to treat human patients for CaP and BPH using a rigid microwave monopole antenna to cause coagulation necrosis.

Saprozink publicly disclosed (Mar. 31, 988) in *Medical Tribune*, "Transurethral Hyperthermia for BPH: Trial's Goal is to Top 80% Success", by Rick McGuire, Thurs., Mar. 31, 1988, pp. 3, 13, 14, a foley catheter built by Astrahan with three EMR antennas, a temperature sensor and a balloon for transurethral hyperthermia for the treatment of BPH.

Turner et al., received U.S. Pat. No. 4,967,765 for a urethral inserted applicator for prostate hyperthermia that contains a single helical coil antenna, temperature sensor means and a balloon.

Hascoat/TechnoMed's European patent application 0 370 890 A1 describes a transurethral catheter with a MW antenna that is positioned with a transrectal ultrasound transducer imaging probe.

Sogawa et al., describes an endotract applicator (U.S. Pat. No. 4,662,383) that employs a balloon to fix a dipole antenna in a tubular organ. The transrectal applicator is shaped to be held in place by the rectal sphincter.

Matsuda's intraluminal applicator described in "Heat Application for Clinical Carcinoma of the Esophagus; Intraluminal hyperthermia for esophageal tumors"; *Hyperthermia Oncology* 1988, Vol. 2, Special Plenary Lectures, Proceeding from the 5th International Symposium on Hyperthermic Oncology, Kyoto, Japan, Aug. 29 Sep. 3, 1988, pp 715–716, employed a balloon with circulated fluid to position the applicator in the esophagus.

U.S. Pat. No. 4,967,765 by Turner et al., discloses the use of a standard foley balloon catheter in the bladder neck to position the transurethral applicator.

Eshel (European Pat. Application 0 248 758) used a balloon on the posterior surface of a transrectal -applicator to push the anterior surface of the applicator against the rectal wall and posterior lobe of the prostate.

Hascoat (European patent application 0 370 890 A1) employed saline filled balloons as a "radio reflective screen" to protect non-target tissues from microwave exposure.

U.S. Pat. No. 5,007,437 by Sterzer used two balloons; one to position the applicator in the bladder neck and a second to compress the tissues during treatment.

None of the above identified patents or publications suggests the use of intracavitary EMR (microwave) hyperthermia (thermal therapy) as a non-surgical approach to endometrial ablation.

SUMMARY OF THE INVENTION

It is an object of the invention to provide an improved treatment for menorrhagia as well as other diseases of the uterus.

Another object of the invention is to provide an EMR applicator apparatus meeting the clinical requirements of a small diameter applicator that can be sterilized and can monitor temperatures generated in the uterine cavity.

These objects are achieved in an electromagnetic radiation applicator apparatus to be routed through the uterine canal and placed within the uterine cavity (intrauterine device) for treatment with hyperthermia techniques to ablate the endometrium. In accordance with the preferred embodiment, the device includes an elongated catheter-like body for insertion into the uterine cavity. The catheter is constructed of a material with a low absorption coefficient such as silicone, with an outside diameter suitable for insertion into a delicate female urethra. The catheter includes a lumen that contains the microwave antenna(s) and sensors for monitoring temperature.

The antenna is integral to the catheter body for propagating electromagnetic radiation. The temperature sensor is mounted on or in the catheter body for detecting the temperature of the tissue surrounding the inserted catheter.

A generator for generating electromagnetic radiation in the microwave frequency range is coupled to the antenna for producing a controlled amount of electromagnetic radiation so that when the catheter is inserted into the uterine cavity, EMR is produced for treatment of the tissue.

Apparatus is provided for monitoring signals from the temperature sensor and controlling the amount of energy propagated by the antenna by varying the output of the electromagnetic energy source to ablate endometrial tissue.

Yet another object of the invention is to provide an transcervical insertable EMR applicator which provides a pear-shaped, uniform EMR heating pattern to enable substantially uniform heating of the endometrium and basalis layer lining the uterine cavity (the uterine cavity is a pear-shaped when distended).

A further object of the invention is to provide a transcervical insertable EMR application which can be positioned within the uterine canal and uterine cavity.

One variation of this invention uses a balloon to fix the applicator in the cul-du-sac of the uterine cavity. In one configuration the balloon is filled with air, in another embodiment it is filled with a non-circulating fluid, and in a third it is filled with a cooled circulating fluid. The balloon serves to provide uniform heating by conforming the cavity to the shape of the balloon, and vice versa. The balloon may also compress tissues, reduce blood flow and thus improve the ability to heat. Physically moving the tissue away from the high intensity near field heating and/or cooling provides more uniform heating to radial depths.

In another aspect of this invention, the balloon or a mechanical means physically moves the antennas out against the sidewalls of the cavity. To that end, a feature of the invention is the physical moving of the antennas (and the temperature sensor(s)) to the side walls of a cavity or tubular organ.

In one configuration of the invention, a helical antenna is curved up and over the tip of the intrauterine cavity, thus assuring heating of the endometrial lining along the uterine fundus. Shifting of the heating pattern can also be achieved by varying the coil windings toward the tip of the antennas or incorporating chokes.

A feature of this invention is the provision of a transcervical EMR applicator, insertable in the uterine cavity, adaptable for endometrial ablation, which provides the generally pear-shaped or inverted tear-drop shaped EMR heating pattern necessary to enable substantially uniform heating of the endometrium and its basilis layer of the uterine cavity and uterine canal.

Another feature of this invention is that a transcervical intrauterine hyperthermia device can be employed to treat medical conditions of the uterus. A still further feature is the provision that the device provides a heating pattern that is consistent in size and shape with the dimensions of the uterine cavity so that relatively uniform heating can be achieved in the endometrium which lines the cavity.

A variation of the invention that mechanically, or with an inflated balloon, moves the antenna out to contact the walls of the cavity is advantageous, as is the use of EMR for endometrial ablation.

One of the objectives of this invention is to uniformly heat the side walls and roof (fundus) of the uterine cavity by employing a intrauterine applicator which propagates EMR and consequently produces heat in a "tear-dropped" or "pear" shape to coincide with the cul-du-sac shaped uterine cavity.

Use of a helical coil design results in more uniform heating along the length of the uterine cavity and the heating pattern does not vary significantly with insertion depth which may vary as the dimension of the cervical as the fundus of the uterine cavity varies between patients.

BRIEF DESCRIPTION OF THE DRAWINGS

Other objects, features and advantages of the invention will become more readily apparent from the following detailed description when read in conjunction with the accompanying drawings, in which:

FIG. 2 is an orthogonal view of a helical-coil microwave antenna and a temperature sensor array, and the positional relationship therebetween;

FIGS. 3a and 3b are respective side and cross-sectional views of a catheter applicator supporting the antennas and temperature sensors therein;

FIG. 4 is a cross-sectional view of another embodiment of the catheter applicator having a cooling jacket therearound for cooling tissue that is in contact with the applicator;

FIG. 5 is a drawing that graphically illustrates tissue temperature as a function of distance away from the catheter applicator, with and without the cooling jacket of FIG. 4;

FIGS. 8b and 8c illustrate respective vertical and horizontal sectional views of a human uterus with isotherms shaped much like the uterine cavity;

FIGS. 8d and 8e are respective horizontal and vertical cross-sectional views of an asymmetric balloon applicator for creating a differential heating pattern in endometrial tissue having a non-uniform thickness;

FIGS. 12a and 12b, when placed together, depict the programmed operations of the medical treatment system of FIG. 1.

DETAILED DESCRIPTION OF THE INVENTION

Figure 1:
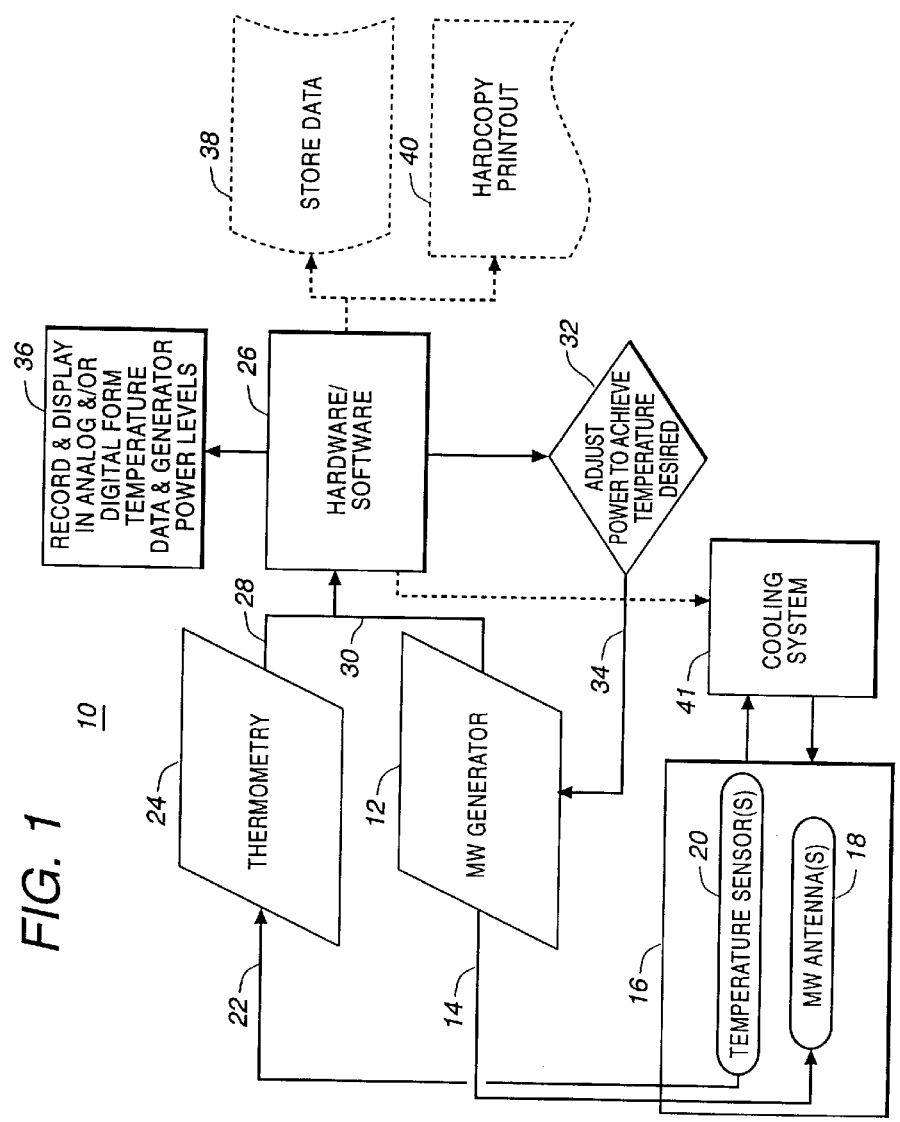
FIG. 1 is a block diagram of the medical treatment system according to the preferred embodiment of the invention.

With reference to FIG. 1, there is illustrated a medical system 10 for the hyperthermia/thermal therapy treatment of various tissue areas of a patient. While FIG. 1 illustrates the basic components according to a preferred embodiment of the invention, those skilled in the art may find other and/or different components may be advantageously utilized, without departing from the spirit and scope of the invention. Also, while the preferred methods and techniques according to the invention employ an applicator that is non-invasive and insertable within a patient's tissue cavity, the apparatus can be employed in other medical applications.

In FIG. 1, there is illustrated a closed-loop treatment system 10 for applying electromagnetic (EMR) energy to a patient, for monitoring the temperature of the patient's tissue affected by the EMR energy, and for coupling indications of both the EMR energy and the tissue temperature to a computer. The computer program achieves and maintains a given temperature of the tissue of the patient being treated based on automatic or manual (i.e. operator controlled) adjustments of the EMR energy. More particularly, the system 10 of FIG. 1 includes an EMR generator 12 for coupling EMR energy via one or more RG-type extension coaxial cables 14 through a splitter and impedance matching device to a catheter applicator 16 having one or more EMR antennas mounted therein.

In the preferred form of the invention, the applicator 16 is insertable in a non-invasive manner in a tissue cavity of a patient, such as a uterus, etc., to provide a thermal treatment to the tissue. As will be described more thoroughly below, the applicator 16 is preferably of a catheter type for insertion in the issue cavity, via a tissue channel of the patient. The applicator 16 also includes formed integral therewith one or more lumen for temperature sensors 20 for measuring the temperature of the tissue being affected by the EMR energy radiated by the antenna 18. In the preferred form of the invention, the temperature sensor 20 is of the type employing fiber optic of fiber-fluoro technology to measure temperature and electronics to convert light transmission/return signals to temperature data. With this arrangement, metallic temperature sensors, such as thermocouples, are not usable, which type of sensors are adversely affected by the EMR energy and thus do not produce reliable temperature data. The analog temperature data is carried by a fiber optic cable 22 to the thermometry equipment 24 for converting the optical, analog signals to corresponding electrical analog signals, and then for converting the electrical analog signals to corresponding digital signals. The thermometry system 24 can provide a digital display of temperatures, or can communicate through an RS232, IEEE, or other electrical communication means to a computer 26. The thermometry equipment is a non-perturbed, fiber-fluoro system providing up to twelve channels that can be configured in any combination of single sensors or four point linear arrays. Such a temperature measuring system 24 can be obtained from Luxtron Corporation, Santa Clara, Calif. It should be noted that additional temperature sensors can be utilized for invasive insertion thereof into tissues (interstitial) or through an intracavitary approach to measure temperatures in target and non-target tissues, should such additional temperature data be required.

Digital temperature data from the thermometry equipment 24 is coupled to a general purpose computer 26, via a data line 28. In like manner, information corresponding to the magnitude of the EMR energy that drives the antenna 18 is coupled from the EMR generator 12 to the computer 26, via data line 30. As can be appreciated by those skilled in the art, an interface (not shown) allows the temperature data and EMR energy data to be processed by a computer 26.

The computer 26 can be a general purpose computer, such as an IBM personal computer, programmed to monitor and control system parameters. To that end, the computer 26 is programmed with software 32 to continuously monitor the temperature data on line 28, compare the measured temperature with a target or prescribed temperature, and provide adjustments to the EMR generator 12 via a control line 34 to thereby increase or decrease the EMR energy to maintain the desired temperature level. The EMR energy provided to the applicator 16 is monitored by the computer 26 by way of the line 30 to assure that certain temperature levels are not exceeded, thus maintaining a safety feature. The computer 26 can be operated, via a keyboard, mouse, or otherwise, to establish various desired temperature and EMR energy levels which, when detected, prevent such level from being exceeded, or cause the computer 26 to shut down the EMR generator 12. The computer 26 is also equipped with a monitor or CRT display 36 for providing a medium to input and output information with respect to the computer 26. In the preferred embodiment of the invention, there is utilized a Windows-based™® software program which allows data to be presented on the CRT 36 in various means, such as graphs, digital readout, analog signal outputs that vary by time, and otherwise. Also, when the CRT 36 is employed in connection with a manually operated mouse (not shown), the user can select and provide input information to the computer 26. The computer 26 is provided with hard-disk drive storage mediums 38 for the nonvolatile storage of patient data thereon. A complete time-based history of both temperature and EMR energy is stored on the medium 38 for each patient, as well as in conjunction with data entered into the computer 26 by the operator. For historical as well as diagnosis/analytical purposes, the data stored on the medium 38 can be retrieved and reviewed by those concerned. In addition, a printer 40 is utilized to provide a hard copy of the data printout, as well as many other parameters stored in either the computer 26 or the hard disk drive medium 38.

The computer 26 can optionally be connected, via the interface, to a cooling system 41 that employs a circulating cooling fluid to control the temperature of either the applicator itself, or the tissue that is situated adjacent the applicator 16.

With reference to FIG. 2, there is illustrated one of the plural EMR antennas employed in the preferred embodiment of the applicator 16. The EMR antenna 18 is constructed of a 50 ohm impedance or equivalent coaxial cable having a center conductor 56, a braided sheath 50 and a Teflon dielectric 52. The proximal end of the coaxial lead is equipped with a standard quick disconnect nanhex or SMA connector 54. A portion of the braided sheath (outer conductor) 50 is removed from the end of the coaxial cable, thereby leaving about 3.5 cm of exposed dielectric 52. The center conductor 56 of the coaxial cable is soldered to a helical coil which is wrapped around the dielectric 52 and in one configuration is connected to the outer sheath 58 and in another is not connected at the proximal end to the outer sheath 58. In the preferred form of the invention, 28 to 35 turns of the helical coil 56 are made around the dielectric 52, with about 1.0–1.5 mm spacing between each turn. With this type of antenna 18, the profile of the EMR energy is generally light bulb or pear shaped, as shown by the broken line 60. Importantly, the antenna of the design shown in FIG. 1 provides the light bulb shaped energy pattern that is relatively independent of the depth to which the antenna is inserted into a body channel or cavity. The shape of the heating pattern produced by the antennas in the applicator is due in part to the frequency of the EMR energy propagated by the generator 12. The generator 12 is a solid state, air cooled unit, producing EMR energy at a frequency of about 915 MHz.

The temperature sensor 20 is shown in FIG. 2 in proximity with the antenna 18, as held by an extruded silicon structure of the supporting catheter (not shown). The temperature sensor 20 preferably includes four optical channels, one shown as reference numeral 70. The end of each fiber is coated with a fluorescent layer 78. The wavelength of the light carried by the optical fiber 70 is changed as a function of the tissue temperature based on the heating of the fluorescent coating 78. Thus, by individually pulsing the optical fibers 70–76 with a specified wavelength of light, the change in the transmission can be detected in the return pulse, and thus the ambient temperature adjacent the fluorescent coating 78 can be calculated. Each of the four optical fibers 70–76 are encased by a support sleeve 80 so that the fibers maintain their relative positions with respect to each other. It is noted that in a linear array each optical fiber is axially spaced relative to one another. With this arrangement, each temperature sensor of the array can monitor the heat generated axially with respect to the active length of the antenna 18. While four temperature sensors are employed in the preferred embodiment, those skilled in the art may prefer that fewer or more temperature sensors be utilized to suit particular purposes. Lastly, the sheathed optical fibers each terminate at an optical connector 82 which mate with a corresponding connector that is connected to an extension cable which, in turn, is connected through optical connectors to the thermometry electronics 24. Temperature sensors of the type described above are commercially available as a Luxtron Fluoroptic thermometer with a two-way RS232 or IEEE-488 port and/or analog port output.

FIG. 3A illustrates one embodiment of an applicator for carrying out hyperthermia/thermal therapy treatments using EMR energy. The applicator 16 shown in FIG. 3A is a significantly enlarged view of the internal construction of the applicator employed for insertion into a tissue channel or cavity. In practice, the applicator 16 is constructed of an extruded silicon catheter 90 with lumen into which the EMR antennas and fibro-optic temperature sensors are placed, and is of sufficient size and length to be insertable into a body cavity, such as the uterus, etc. In practice, the applicator 16 is about 7.0 mm in diameter and about 70 cm long, with the various antenna coaxial cables and optical fibers extending from one end (not shown) thereof. The extruded silicon catheter 90 is advantageous as it is biocompatible, is relatively inexpensive and easy to manufacture. Indeed, in the preferred form of the invention, the silicon catheter 90 is disposable, in that the various EMR antennas 18 and the temperature sensors 20 are removable from the silicon catheter body 90 and may be reusable. To that end, the silicone catheter body 90 is extruded to form therein a number of tubular conduits (lumen) therethrough, such as shown in the cross-sectional view of FIG. 3B. One conduit 92 is shown in FIG. 3B, with others spaced around a central conduit 94 that also extends the length of the catheter body 90. Three conduits 96, 98 and 100 are annularly spaced from each other 120°, and have inserted therein the respective EMR antennas 18*a*, 18*b* and 18*c*. Three other conduits are formed through the catheter body 90, one conduit 102 having inserted therein the four-point array temperature sensor 20 shown in FIG. 2. It can be appreciated that the remaining vacant catheter conduits 92 and 104 can accommodate other EMR antennas, thermometers instrumentation sensors, the flow of a cooling medium therethrough, or to inflate a balloon or balloons. Indeed, those skilled in the art may prefer to rearrange the location of the antennas and/or measurement sensors to achieve particular radiation patterns, or to achieve other advantages.

The various conduits have a diameter somewhat larger than the diameter of the respective EMR antenna or temperature sensor, thereby allowing these items to be easily inserted or withdrawn from the catheter body 90. Preferably, each antenna 18a–18c is inserted to the extent that the tips or ends thereof are aligned to thereby provide the light bulb shaped radiation pattern 60 shown in FIG. 2. The linear array temperature sensor 20 in inserted within its conduit 102 so that its end of temperature sensor array is placed in a location such that the individual sensors therein are spacially located in a strategic position to monitor temperature. Antennas are positioned in the desired arrangement and secured by heat shrinkable tubing at the proximal end of the applicator to prevent relative axial movement of the antenna (s).

With specific reference to FIG. 3B, there is also illustrated the central conduit 94 that has insertable therein a rather rigid rod-like trocar 106. For purposes of clarity, the center structure shown in FIG. 3B is not shown in FIG. 3A. The trocar 106 is temporarily inserted in the center conduit 94 of the catheter body 90 to provide rigidity and a slight curvature and thereby enhance insertability into body cavities. The trocar 106 is preferably constructed of a nonmetallic material. Those skilled in the art may realize that a catheter can be constructed of a more rigid material which would eliminate the need for a trocar.

As noted in FIG. 3A, the silicon catheter body 90 terminates in a rounded or conical tip 108 to also facilitate placement into a tissue channel. As will be explained in more detail below, the ability of the applicator 16 to be insertable into a tissue channel allows thermal EMR treatment of the surrounding tissue.

FIG. 4 illustrates an applicator 110 that can be constructed in a manner similar to that shown in FIG. 3B, but additionally with an outer annular cooling jacket 112. The outer cooling jacket 112 can be made with a silicone material, rubber, PVC, or other suitable material. The cooling jacket 112 may include plural webs 114 for supporting the jacket 112 with respect to the catheter body 90. As can be seen in FIG. 4, an annular space 116 exists between the outer surface of the catheter body 90 and the inner surface of the cooling jacket 112. A cooling medium, such as air, water, etc., can be pumped through the annular space 116 to remove the heat generated in tissues in contact therewith, which heat is generated by the conversion of the EMR energy emitted from the antennas 18 and absorbed by the body tissues. Those skilled in the art may find it preferable to construct the webs 114 so as to provide isolated and independent fluid channels 116. With this arrangement, a cooling medium can be pumped or otherwise circulated in one direction in one channel 116, and returned in another direction in another channel. In order to accomplish this, the distal ends of the annular cooling channels 116 can open at the tip 108 (FIG. 3A) of the catheter body 90 into a common chamber such that a return path is made to the other exit fluid channels. When connected to the cooling subsystem 81, certain ones of the cooling channels 116 can be connected to the output end of the cooling pump, while other channels can be connected to the return inlet of the pump.

Depending upon the type of cooling medium employed for circulation in the applicator 110 of FIG. 4, such fluid may generate heat directly from the EMR energy absorbed thereby, especially if the medium is a liquid such as water. This, of course, requires that the total EMR energy be increased in order to achieve a specified tissue temperature at a predefined radial distance from the applicator 110. However, by utilizing the cooling chambers 116 of the catheter, the tissues directly adjacent thereto can be cooled by removing heat therefrom by conduction to the circulating cooling fluid. As a result, the EMR energy of the applicator 110 can be increased to thereby increase the temperature generated in tissues spaced further away from the applicator 110, without overheating the tissue that lies directly adjacent the applicator 110. It is well known that the EMR energy radiated from an antenna into a medium with an absorption coefficient, like muscle, will generate heat which rapidly falls to a baseline temperature with increased radial distance. As a result, the intensity of the EMR energy closer to the applicator is greater, thus heating the tissue that lies closer to the applicator to a higher temperature. In sum, by the use of a catheter having a cooling jacket 112, remotely located tissues can be heated to a higher temperature without overheating the tissue that lies directly adjacent the applicator, as would be the case without the cooling jacket 112.

FIG. 5 illustrates the tissue temperature profile of an applicator 110 with a cooling jacket 112, and an applicator without such type of jacket. The graph of FIG. 5 illustrates along the vertical axis the temperature of the tissue heated by the EMR energy, and the horizontal axis illustrates the distance of the tissue away from the applicator 110. Moreover, the graphical line 120 illustrates the temperature profile of thermal energy in body tissues generated by an applicator 90 without a cooling jacket, such as the type shown in FIG. 3B. On the other hand, line 122 illustrates the temperature profile of tissues in which the thermal energy is imparted thereto with a applicator 110 having a cooling jacket 112, such as the type shown in FIG. 4. In the graphical analysis there is shown the temperature profile of tissue in which the thermal energy is imparted thereto with a applicator 110 having a cooling jacket 112, such as the type shown in FIG. 4. In the graphical analysis of the temperature profiles, it is seen that an applicator without a cooling jacket 90 can achieve a very high temperature in tissues directly adjacent the applicator, with the temperature gradient decreasing as a function of distance away from the applicator. In contrast, the graphical line 122 illustrates that the thermal energy generated in tissues directly adjacent the applicator is reduced, due to the portion of the thermal energy being conducted to the cooling medium and thus removed from the adjacent tissue. Importantly, it can be seen from the graphical analysis of FIG. 5 that for tissues of a given distance from the EMR applicator 110, the tissue temperatures are higher when employing an applicator with a cooling jacket 112, and the tissues directly adjacent the applicator 110 are not overheated.

Figures 6A, 6B:
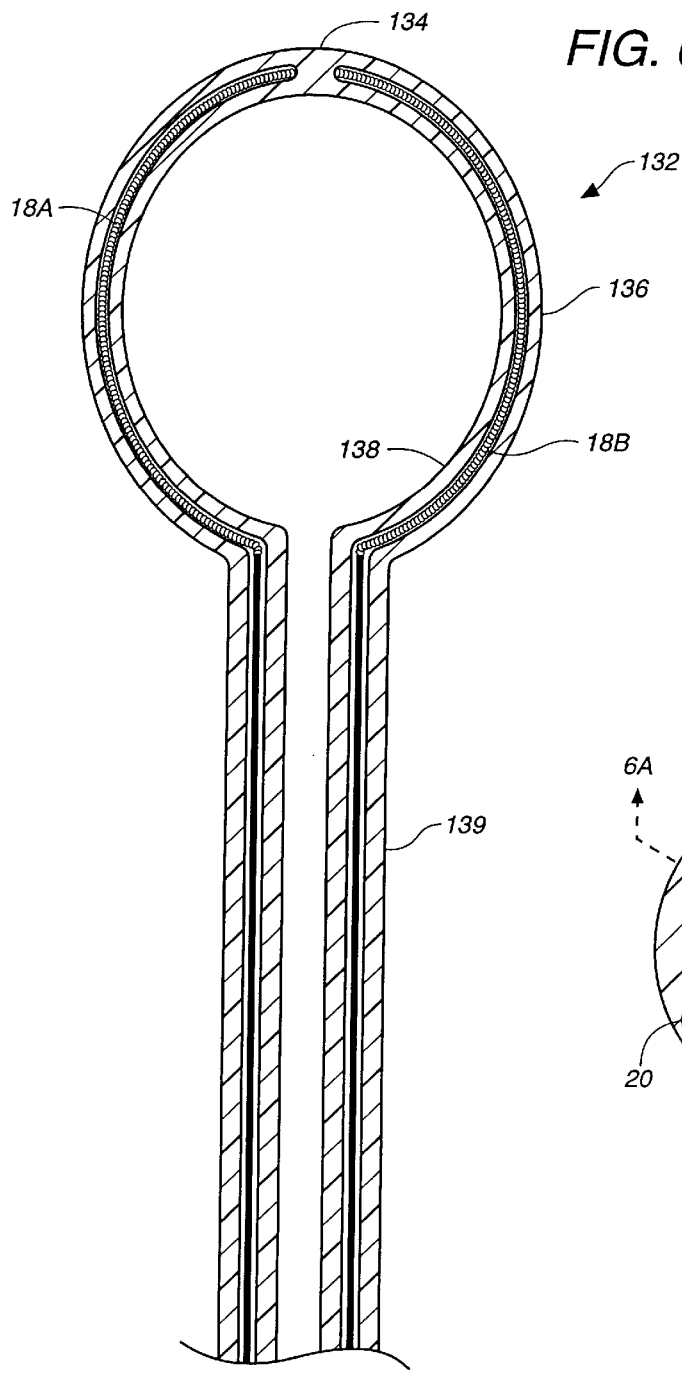
FIGS. 6a and 6b are respective side-sectional and cross-sectional views of a balloon-type catheter employing plural antennas and a temperature sensor.

With reference to FIGS. 6A and 6B, there is illustrated another applicator 130 that is equipped with a balloon at the distal tip of the applicator. The balloon 132 can be inflated with air or fluid after the insertion of the applicator 130 into the body cavity, such as a uterine cavity. The major advantage of the balloon 132 is that it physically moves the antennas and temperature sensors with it as it inflates out to remain in contact with the cavity wall. In other words, once the balloon applicator 130 is inserted and placed in the proper position within the cavity, the balloon 132 can be inflated to thereby prevent axial movement of the applicator within the cavity. Several other advantages are readily apparent for the thermal therapeutic treatment of the uterine endometrium tissue with a balloon-type applicator 130. For example, when the balloon catheter 130 is expanded in the uterine cavity, the sidewall tissue of the cavity stretches somewhat and conforms to the shape of the balloon catheter as shown in FIG.6A. This expansion forces conformity of the uterine wall tissue to the shape of the balloon to provide a uniform thermal treatment of the uterine tissue. Moreover, and as noted above, the light bulb EMR pattern is generally similar to the shape of the expanded balloon 132, and thus facilitates the thermal destruction of the desired endometrium tissue which has also been forced to such shape. As will be described below, this technique facilitates the uniform ablation of the endometrial tissue of the uterine cornus. Another advantage of the utilization of the balloon catheter 130 is that the EMR antennas 18 are inserted in the respective conduits which terminate near the tip 134 of the balloon catheter 130. In this manner, the radiated electromagnetic field near the ends of the respective antennas uniformly heats the uterine tissue adjacent the distal tip 134 of the balloon catheter 130. The end result is that when the balloon catheter 130 is expanded, the uterine wall is forced to a contour or shape that conforms to the EMR pattern. The endometrium tissue lining the uterus can thus be more uniformly and completely destroyed without destroying the underlying tissue. A further advantage is that the balloon 132 can be pre-shaped so that it expands and causes the body cavity to conform to the shape of the balloon, thus providing a "eform" to which the body cavity is conformed. This forces the tissue to a consistent and repeatable shape that coincides with the heating pattern of the antennas 18.

Another advantage of the balloon catheter 130 is that during expansion thereof, it compresses the body tissues, thus reducing blood flow therein, and in turn increasing the efficiency by which thermal heat is transferred to the tissue to be ablated. In other words, the normal flow of blood through tissues is effective to carry away a certain amount of heat. This represents an inefficiency in heating the tissue to the desired temperature. Cooling by vaso-dilatation is thereby prevented, insofar as the blood vessels are compressed, thereby reducing the blood flow therethrough and reducing the amount of thermal energy removed from the tissue by the blood flow.

The construction of the basimon catheter 130 is similar to that shown in FIGS. 3A and 3B, in that plural EMR antennas are insertable into the respective conduits, and other conduits may be employed for instrumentation sensors, such as temperature sensors. It should be understood that the greater the number of EMR antennas employed, the more uniform heating there is around the uterine wall. Moreover, the silicone catheter body 136 near the end of the catheter, i.e., the balloon portion 132, is thinned so that when a liquid is injected or forced into the internal catheter cavity 138, only the end of the catheter 130 expands, and the remaining elongate portion 139 of the catheter does not expand. This nonuniform thickness of the balloon sidewall can thus provide a non-symmetrical shape to match the shape of the body cavity. Antenna configurations can also be utilized to produce radiation patterns that match the non-symmetrical shape of the balloon portion of the applicator. The internal sidewall 138 of the catheter prevents the expansion fluid injected therein from coming into contact with either the EMR antennas 18 or the temperature sensors 20 and the patient's tissue. After the thermal therapeutic treatment has been completed, the balloon catheter 130 can be deflated and removed from the tissue channel by pulling the applicator. While not shown in FIG. 6A, the balloon catheter 130 can be constructed with an additional, isolated internal central conduit 94 for insertion therein of a malleable trocar 106, much like that shown in FIG. 3B. This can facilitate the insertion of the balloon catheter into a pliable body cavity. Should it be necessary to provide EMR energy radiation at other locations along the balloon catheter applicator 130, the EMR antennas 18 can be unclamped at the base of the catheter thereof, and pulled out of the respective conduits a distance sufficient to position the antennas at the desired axial location along the catheter 130. Then, the EMR antennas 18 as well as the temperature sensor 20 can be clamped by heat shrinkable turning, or the like, to maintain the respective positions. Those skilled in the art may realize that the various features of the invention may find particular uses and advantages in other applications.

Figure 7:
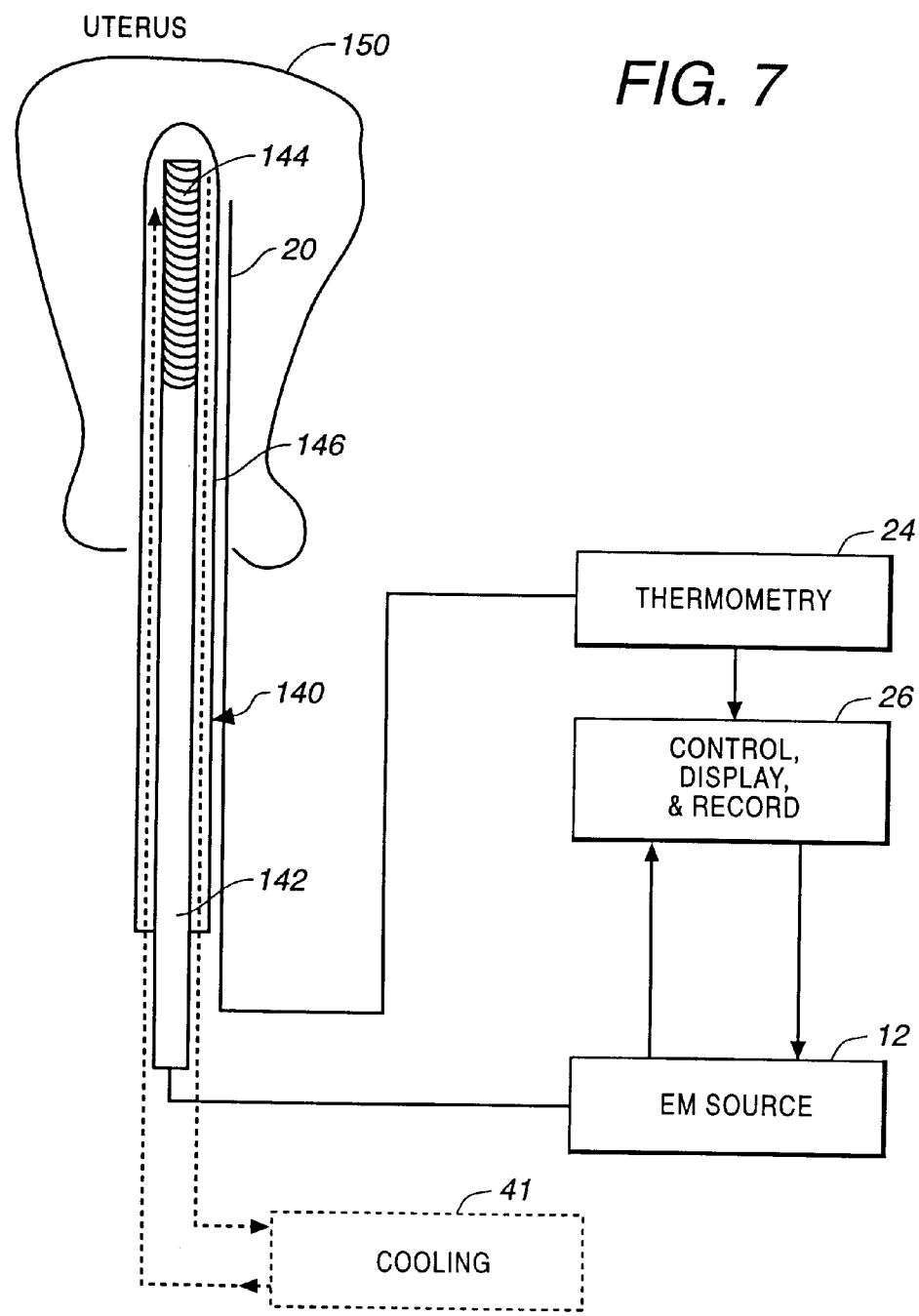
FIG. 7 is a generalized diagram of a transcervical intrauterine EMR applicator system employing a single antenna.

As noted above, the invention is particularly well-adapted for trans-cervical, intrauterine thermal therapy to ablate endometrial tissue. With reference to FIG. 7, there is illustrated another embodiment of an applicator 140. In this embodiment, the applicator 140 includes a catheter body 142 and one antenna 144. The applicator 140 includes an outer jacket 146 for circulation therethrough of a cooling medium. The cooling medium is circulated through the applicator 140 by way of a cooling system 41. The cooling system 41 includes a pump which may be of the peristaltic type, and a heat exchanger for removing thermal energy from the cooling medium. The thermometry equipment 24 is illustrated with the temperature sensing probe 20 shown adjacent the applicator 140. In accordance with an important feature of the invention, the applicator 140 is shown inserted within the cavity of a uterus 150. As noted above, the endometrium layer within the uterine cavity can be heated sufficiently so as to be destroyed and thereby prevent uterine complications. The thermal therapeutic treatment of the endometrium tissue will be described below in connection with the software controlled operation of the system 10.

Figure 8A:
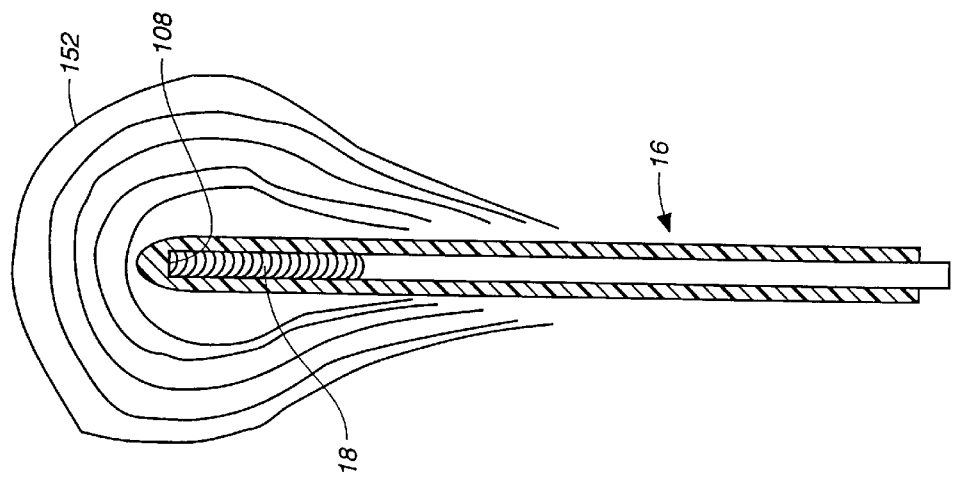
FIG. 8a is a drawing of the light bulb shaped heating pattern based on specific absorption rate (SAR) measurements taken in muscle equivalent phantoms and confirmed by animal (pig) and human interstitial temperature measurements.

In FIG. 8a, the shape of the heating pattern is shown as isotherms that result from the emission of EMR energy from the antenna 18 of an applicator 16. As clearly shown, the heating pattern 152 is light bulb shaped, which is similar to the shape of the uterine cavity, whether or not the applicator 16 is of the balloon type. Also, and as noted above, the intensity of the heat generated adjacent the EMR antenna 18 is greatest, and decreases by the inverse square as a function of distance away from the antenna. Such type of thermal energy pattern is well adapted for thermal endometrial ablation of the uterine cavity. Further, it is noted that the heating pattern 152 extends outwardly from the tip 108 of the applicator 16 as a result of the helical antenna coil winding. The radiation heating pattern therefore contrasts with the dipole-type of antenna and other types known in the art.

FIG. 8b illustrates an applicator of the balloon catheter type inserted into the cavity 151 of a uterus 153. The balloon portion 154 of the applicator 16 is shown expanded by a fluid so as to conform the endometrial layer 155 of the uterus 153 to the shape of the electromagnetic pattern 152. The endometrial layer of tissue varies in thickness depending on the patient and a number of other factors, but is generally in the neighborhood of 2 to 10 mm (depth per side wall). By conforming the endometrial layer 155 of tissue to the radiation pattern 152 of the antenna 18, such tissue layer can be uniformly ablated without substantially affecting the myometrium layer of the uterine tissue. Based on experimental results, the time required to ablate the endometrium layer 155 as a function of temperature can be carefully and reliably determined.

While a pear-shaped electromagnetic radiation pattern 152 of the antenna 18 is highly effective to ablate the endometrial tissue 155 without the use of a balloon catheter, the balloon 154 also functions to conform the cavity to the shape of the balloon and compress the uterine tissue. In certain instances, tissue stretching may occur. The surface compression of the endometrial layer 155 serves to reduce the blood flow therein and produce a corresponding reduction in the thermal energy loss of such tissue. The ablation efficiency is thereby enhanced.

FIG. 8c illustrates a horizontal cross-sectional view of a uterine cavity 151, as distended by a balloon catheter type applicator 16. Importantly, FIG. 8c shows a cross-section through the cornus 156 of the uterus 153. The cornus 156 is that part of the uterus 153 where the fallopian tubes open into the uterine cavity 151. The potential uterine cavity is widest from the right to left cornus 156 and these distant "pockets" are collapsed on themselves in their non-distended natural state. The endometrial layer of the cavity extends up into the cornus 156 where it thins and terminates. Failure to effectively reduce or eliminate menorrhagia when laser or electrosurgical techniques are employed is frequently attributed to their inability to mechanically reach the cornus and ablate the endometrium therein. When an abnormally wide cavity is identified, the propagation/heating pattern of the non-distended applicator may not be sufficient to elevate temperatures to ablative levels in the distant cornus. In this case, utilization of the distention applicator assures that the cornus are mechanically opened and are moved into and against the surface of the balloon 154. This assures that the cornus are moved within the propagation/heating pattern and that uniform thermal treatment is provided to all regions of the endometrial layer 155.

FIG. 8d illustrates yet another technique for thermally treating the uterine tissue. When using this technique, the endometrial lining of the uterus is of nonuniform thickness, and is treated with a differential heat pattern. It often occurs that the thickness of the anterior endometrial lining 250 is between 4–6 mm, whereas the thickness of the posterior lining 252 is 9–12 mm. In this situation, a uniform thermal treatment may fully ablate the anterior uterine lining 250 but not the posterior lining portion 252. If the depth of heating is adjusted so that the posterior lining 252 of the uterus is fully ablated, then the myometrium tissue located at the anterior portion of the uterus may be over heated.

The non-uniformity of the endometrial lining thickness can be fully ablated by providing an asymmetrical EMR energy density to the endometrium tissue. This can be understood by reference to FIGS. 8d and 8e where there is shown a uterus 153 having a thick posterior endometrium lining 252 and a thinner anterior lining 250. Also shown is an applicator 254 having a balloon portion 256 expandable by a gas or liquid. The balloon 256 can be constructed in a manner similar to the balloon catheters that are fabricated for angioplasty procedures. The balloon applicators 254 according to the invention are formed in a similar manner, but with the balloon portion 256 offset with respect to the tubular shaft portion 258. With this arrangement, when the microwave antenna 260 is inserted into the tubular shaft 258 so that the antenna coils are disposed within the balloon portion 256, the axial axis of the antenna 260 is offset with respect to the locus or center of the balloon 256. As can be appreciated, the density of the microwave energy near the posterior portion of the balloon 256 is greater than the EMR energy near the anterior portion of the balloon 256. The distance or length of the offset 262 is preferably related to the difference between the thickness of the anterior 250 and posterior 252 portions of the uterus 153. If the thickness of the endometrium lining is uniform, then the offset 262 is minimal or zero. As the difference between the thickness of the anterior and posterior lining increases, as between different patients, then the offset 262 is greater. Typically, with a balloon diameter of about 14 mm and an antenna diameter of about 7 mm, a nominal offset of about 3.0 mm is acceptable for treating differential lining thicknesses of about 5 mm. The offset 262 is measured from center to center of the balloon portion 256 and the antenna 260.

As noted above, the asymmetrical applicator 254 can be constructed with a balloon 256 much like angioplastic catheters are constructed, but with different molding techniques. A conventional polymer can be utilized in constructing the balloon portion 256 of the applicator 248. As is well known, a balloon constructed of such material has the characteristic such that when fully inflated, the shape and size are predetermined and when inflated, expand to fixed dimensions and cannot be expanded further.

A mold is fabricated for forming the asymmetrical balloon applicator 254. The part of the mold utilized in forming the balloon portion is offset a defined distance from the mold part in which the tubular shaft 258 is formed. When the applicator 254 is removed from the mold and inflated, the axis of the tubular shaft 258 is offset from the locus of the balloon portion 256, as shown in FIG. 8e. Those skilled in the art can utilize other balloon shapes, or utilize plural antennas, each disposed within the balloon portion 256 at a different location to produce desired energy densities around the circumference of the balloon. A differential heating can thus be provided in the surrounding tissue to accommodate different tissue thicknesses, consistencies, etc.

Figures 9A, 9B:
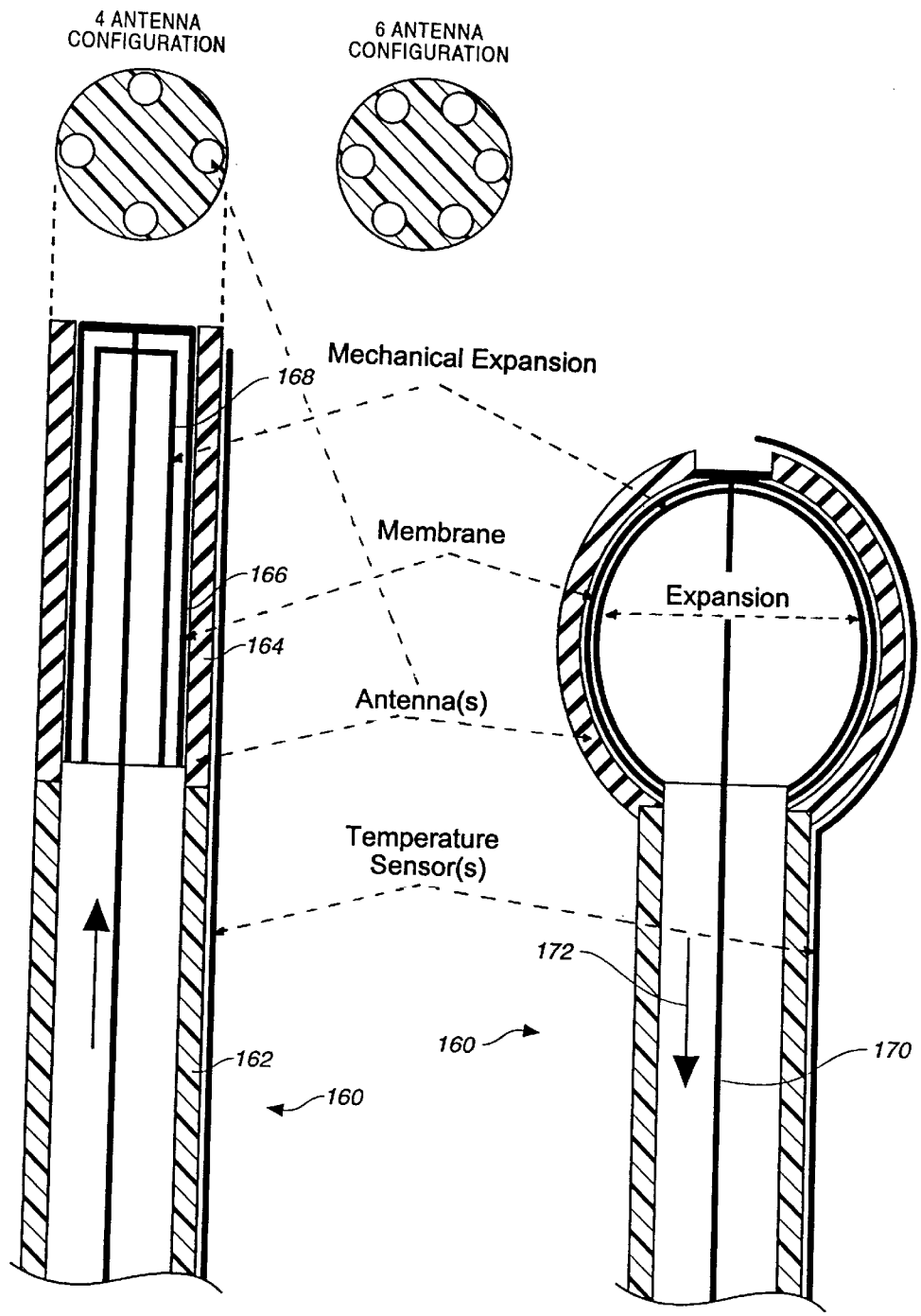
FIGS. 9a and 9b show sectional views of the transcervical intrauterine EMR applicator system in both an uninflated and inflated condition in which the antennas are moved by expansion from a mechanical structure, and cooled fluid is circulated within a membrane covering the mechanical structure and antennas.

Referring now to FIGS. 9A and 9B, there is illustrated yet another embodiment of a balloon-type applicator 160. The balloon catheter 160 is shown in a non-inflated state in FIG. 9A, and is shown inflated by a mechanical mechanism in FIG. 9B. The balloon catheter 160 includes an extruded silicone body 162, a base portion of which is not expandable, and an upper portion 164 that is expandable by the mechanical mechanism. While not shown, preferably four or six EMR antennas 18 are spaced equidistantly around the silicone catheter material 164 in conduits much like that described above. A membrane 166 is formed inside the balloon portion of the catheter. Preferably, a non-metallic mechanical structure 168 can be employed to physically expand the balloon portion 164 after insertion into the uterine cavity by moving a rod 170 in the direction shown by arrow 172 in FIG. 9B. This mechanical expansion of the balloon catheter moves the antennas and the temperature sensor radially outwardly against the walls of the uterine cavity. This configuration employs the centrally located rod 170 which, when in the extended position, retracts the antennas 18 and temperature sensor 20 against the catheter body for easy insertion or removal from the uterine canal. When the central rod 170 is retracted, the mechanical structure is expanded, whereby the antennas 18 and the temperature sensor 20 are physically moved away from the catheter body and against the internal wall of the uterine cavity.

Figure 10:
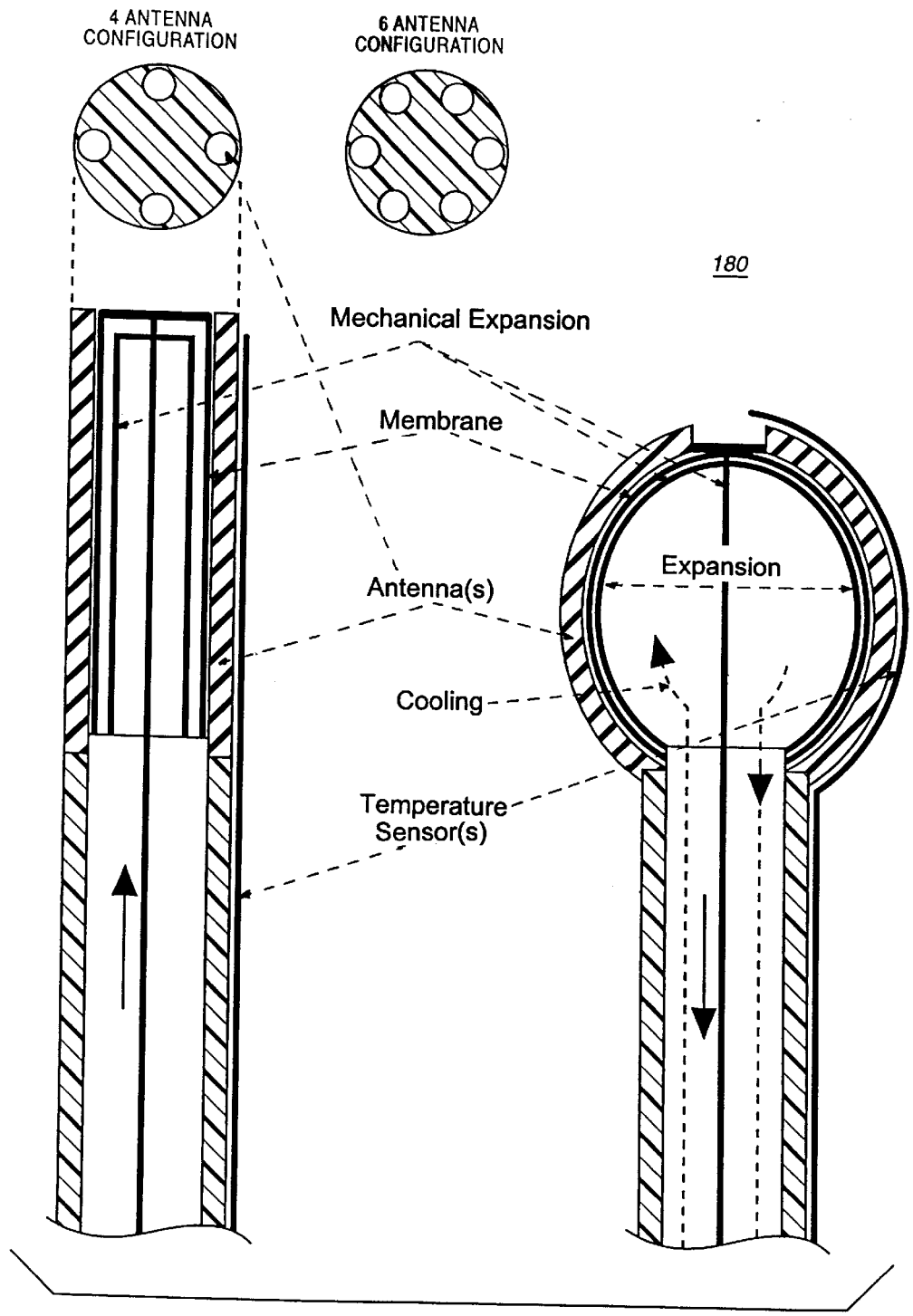
FIG. 10 is a view of the transcervical intrauterine EMR applicator system similar to that shown above in FIG. 7, but with a view of the applicator inflated in which the antennas are moved by expansion from a mechanical structure.

Referring now to FIG. 10, there is shown a balloon catheter 180 that is structurally similar to that described above in conjunction with FIG. 9, but is further adapted for allowing the circulation of a cooled air medium or fluid through the expandable balloon portion thereof, or through the mechanical expansion apparatus. By covering the mechanical expansion area of the catheter body with a balloon material or membrane which is sufficiently flexible to expand and thereby move the EMR antennas outwardly against the wall of the cavity, a cooled gas (air) or a cooled fluid (water) can be circulated therein to lower the temperature of the tissue that is in direct contact with the surface of the applicator 180.

It should be understood that in the various catheter applicator embodiments described above which utilize multiple EMR antennas to provide a relatively uniform heating pattern in a transverse direction to the applicator, other EMR antennas can be staggered relative to the distal tip of the applicator, with the respective distal tips of the antennas varying in their distance from the tip of the catheter. Alternatively, the space between the coil windings of each individual antenna can be varied to also achieve a different heating pattern. Either approach achieves substantially the same result of reducing high intensity (EMR field) areas where the antennas are in close proximity to the distal tip of the applicator, or low intensity areas where the antennas are separated one from one another when the applicator is in an expanded condition.

Figure 11:
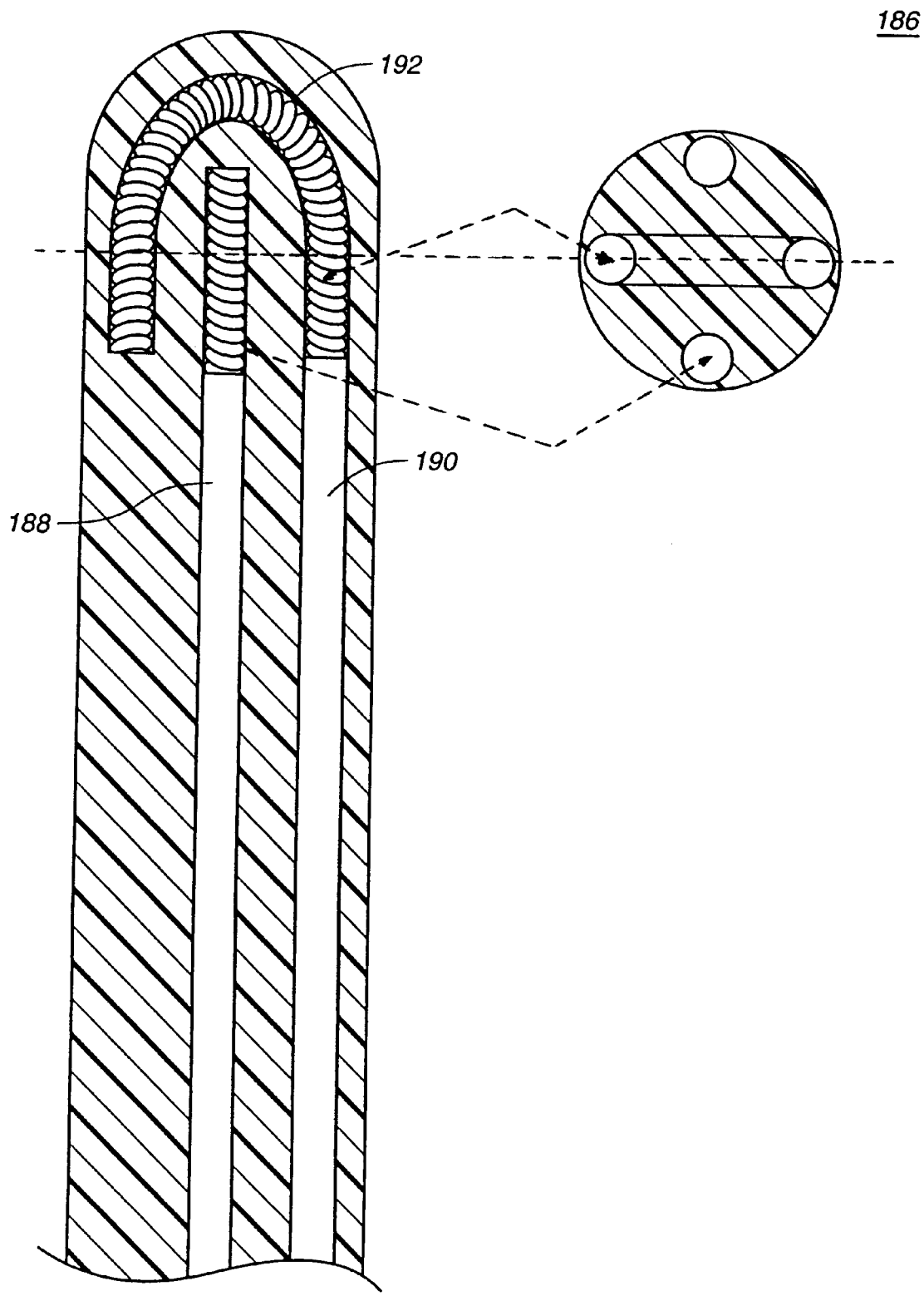
FIG. 11 illustrates another embodiment of a catheter applicator having an antenna that curves over the distal tip to provide electromagnetic radiation directed outwardly from the tip.

Referring to FIG. 11, there is illustrated yet another embodiment of an applicator 186 having an EMR antenna configuration that provides an enhanced EMR energy pattern extension outwardly from the distal tip of the applicator. Like many other of the embodiments disclosed herein, the applicator 186 includes plural EMR antennas, with one or more antennas 188 extending axially along the side of the applicator 186. However, in this embodiment there is provided an antenna 190 that is curved laterally around the tip or crown of the applicator, and then downwardly a short distance on the opposite side of the applicator. In this manner, the EMR energy radiated outwardly from the midsection of the curved antenna 190 extends away from the distal tip of the applicator, thereby providing thermal energy in the tissue adjacent thereto. While FIG. 11 illustrates only one such curved antenna 190, additional antennas can be formed with similar semicircular curves. Indeed, other EMR antennas may only extend upwardly near the tip of the applicator 186 and terminate adjacent the apex of the semicircular portion 192 of the EMR antenna 190. Those skilled in the art may prefer yet other configurations, shapes or sizes of EMR antennas to provide other distinct and/or specific radiation patterns.

Figure 12B:
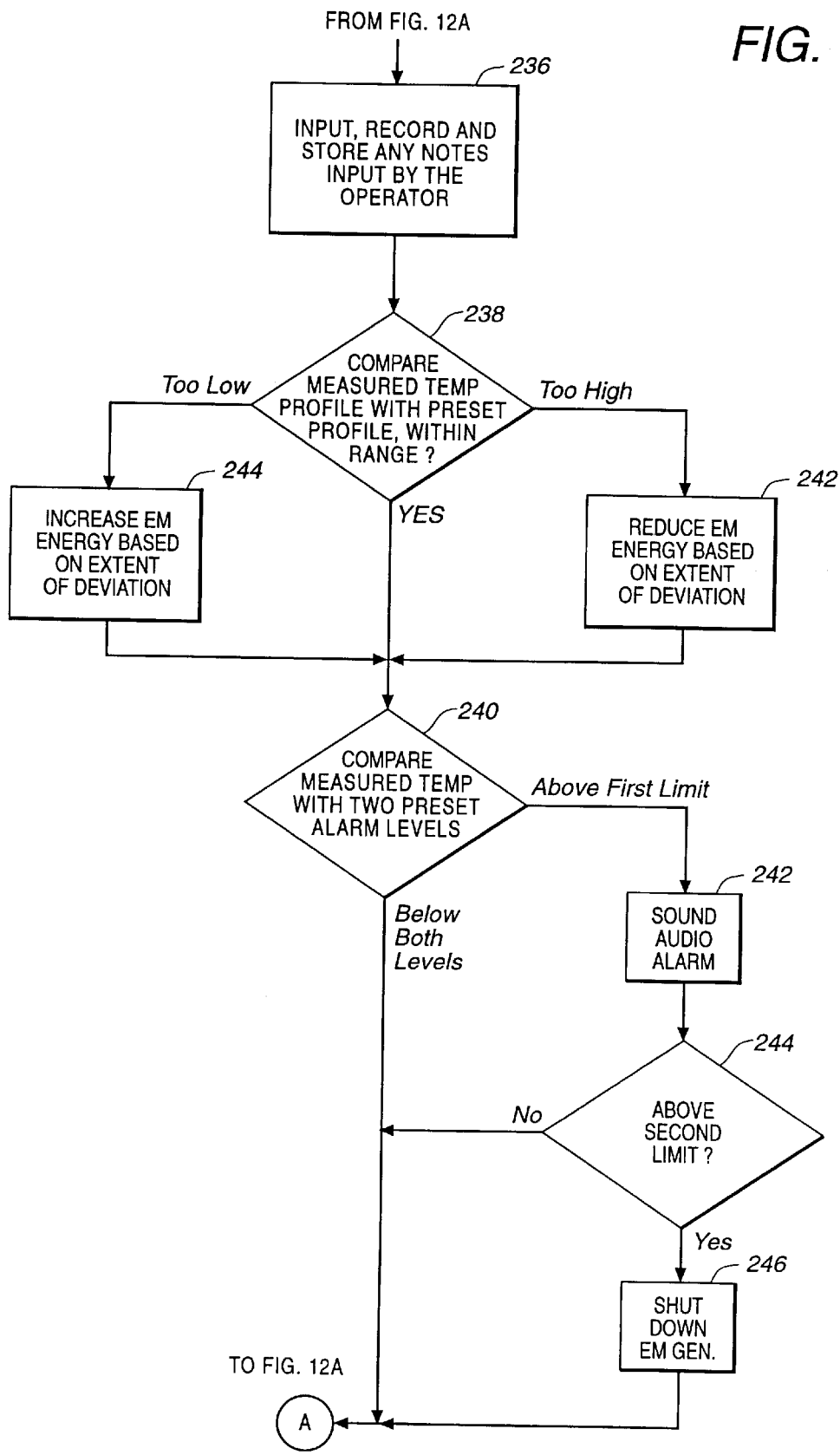

FIGS. 12A and 12B illustrate the basic programming 200 of the computer 26 for carrying out the thermal treatment utilizing the applicators described above, or other types of thermal treatment systems. In the flow chart 200, the start of the computer and program is initiated by the operator, whereupon various registers, memory areas, etc., are initialized. In addition, various diagnostic routines can be carried out to ascertain the functionality of the hardware, as well as to verify the correct connection of the equipment to the computer interface. In program flow block 210, there is displayed on the CRT 36 various prompts and instructions for the operator to choose temperature and EMR energy parameters, profiles, etc., or to manually press on the screen an underlying image and select the desired parameters or profiles. In program flow block 212, the computer 26 receives data input via the keyboard, mouse or otherwise, patient information and any other relevant medical information to provide a complete treatment record of the patient. The software may include various routines for establishing preprogrammed profiles for initially increasing the EMR energy to a desired treatment level. This is shown in program flow chart 214. In other words, it may be desirable not to start the EMR generator 12 at the full desired energy level, but rather to periodically increase the energy in steps over a period of time until the desired energy level is received. Next, and as shown in program flow block 216, there is established in the computer 26, by way of preset levels, or inputs via the operator, at least two safety temperature operating levels. A first level is established such that if the temperature of the tissue being treated rises above such level, audio and visual alarms are activated to alert the operator thereof. Various additional visual alarms can also be triggered when the first safety temperature level is exceeded. A second tissue temperature level is established such that, if exceeded, the computer 26 causes the EMR generator 12 to shut down and prevent undesired tissue damage due to dangerous temperatures. Also shown in program flow block 216, the two safety levels are displayed on the CRT 36 as two horizontal lines, below which the analog temperature of each sensor of the array of temperature sensors 20 is displayed as a function of time. The analog temperature is thus displayed graphically in real time for continuous visual monitoring by the operator.

In program flow block 218, the EMR generator 12 is started as a time clock. The time clock is incremented every five seconds to provide a time parameter associated with the temperature and EMR energy level data as well as for incrementally updating the analog graphical indications. From program flow block 218, processing proceeds to decision block 220, where the temperature sensor 20 is monitored via the thermometry equipment 24. If the tissue temperature exceeds a preset level, then the cooling subsystem is started, as noted in program flow block 222. If the circulation of a cooling medium is not required, program flow continues to block 224 where the EMR energy level and the tissue temperature are recorded, as input to the computer 26 via lines 28 and 30. The temperature and energy levels associated with the time parameter are stored as data for later retrieval, if necessary. The computer 26 graphically displays the analog temperature information of all the probes 20 of the array as a function of time, and also stores the results as data. This is shown in program flow block 226. Here, if there are four temperature sensors in an array of the probe 20, then four analog lines will appear on the CRT 36 as a function of time, showing the actual temperature as measured by each probe. In carrying out the instructions of program flow block 228, the computer 26 also graphically displays the temperature profile in color gradients as they exist around the applicator 16. The temperature profile may appear similar to that shown in FIG. 8, but with the different isotherms shown in different colors.

Program flow block 230 causes various treatment parameters to be digitally displayed on the CRT 36, such as the temperature as measured by each sensor of the probe 20, the EMR energy, the time, the patient's name, etc. In program flow block 232, the EMR energy is also displayed in an analog level, via an analog needle that points to a number corresponding to the EMR energy in watts. In program flow block 234, the EMR energy reflected in each coaxial cable 14 connected to the various EMR antennas 18 is measured and displayed. In carrying out the instructions of program flow block 236 (FIG. 12b), the computer inputs, records and stores any other data or notes input by the operator.

With regard to the program flow block 238, the computer 26 compares the measured temperature with the preset temperature profile to assure that the tissue being treated is heated according to a desired temperature profile. If the measured temperature is within the specified range of the preset profile, processing proceeds to decision block 240. If, on the other hand, the comparison that is carried out in decision block 238 indicates that the measured temperature is higher than the profile temperature, processing branches to block 242 where the EMR energy of the generator 12 is incrementally reduced. The energy output of the generator 12 can be reduced according to a predefined rate, based on the extent of deviation between the measured and preset temperature profiles. In like manner, if the comparison as a result of decision block 238 determines that the measured temperature is too low, processing branches block 244 where the EMR energy is increased, based on a rate determined as a function of the deviation between the measured and preset temperature levels.

From program flow blocks 238, 242 or 244, processing continues to the decision block 240, where the measured temperature is compared with the two preset alarm levels established in block 216. If the comparison as a result of decision block 240 determines that the measured temperature is below both alarm levels, then processing returns to block 224 and continues with the closed-loop control of the thermal energy utilized in treating the patient's tissue. If, on the other hand, the measured temperature is not below both alarm levels, processing branches to block 242 where the audio alarm is sounded. Further, another decision is determined in block 244, namely whether the measured temperature is above the second alarm limit. If the measured temperature is not above the second alarm limit as established in program flow block 216, processing returns to block 224 where the closed-loop operation continues. However, if the measured temperature is at or above the second alarm limit, as determined by decision block 244, processing branches to block 246 where the EMR generator 12 is shut down. From block 246, processing branches to block 224 where the energy, temperature and other parameters continue to be measured and recorded as a function of time. While not shown, processing exits the closed-loop operation by intervention of the operator, via the mouse and/or keyboard of the computer 26, or automatically after a predetermined period of time.

Those skilled in the art may find that many other arrangements of the processing described above are possible, and many other additions thereto may facilitate or enhance the thermal therapeutic treatment of patient tissues.

In accordance with a method of the invention, a transcervical intrauterine silicone applicator is employed in the thermal therapy and management of menorrhagia to ablate the endometrium tissue of a uterus. The heat generated in the tissue by the absorption of EMR energy elevates the endometrium and basal layer to temperature levels that cause irreversible thermal damage, thus preventing regeneration of the endometrial tissue at the next menses. In accordance with an important feature of the method, the ablation of the uteral endometrium is uniform, because the heating pattern of the applicator corresponds to the shape of the endometrial cavity that is confined to the uterus, thus minimizing any thermal damage to extra-uterine tissue. In accordance with the method, the patient is placed in a dorsosacral position under general anesthesia. After cervical dilation and sounding to determine the length of the uterine cavity, the transcervical uterine EMR applicator is positioned therein using a centrally placed trocar 106 held in place with a single tooth tenaculum or other mechanical means, or if a balloon configuration is utilized, the inflated balloon in the uterine cavity affixes the applicator in place. Preferably, although not necessary, an applicator of the type having three omnidirectional helical coil EMR antennas and a four-point linear array fiber-optic temperature sensor is utilized.

EMR energy is then supplied to the applicator, whereby the three antennas radiate the EMR energy in the light bulb shaped pattern to thereby uniformly heat the endometrium tissue. Preferably, the EMR power is incremented in the initial phase until the desired operating temperature is reached, as measured by the temperature sensors 20. Preferably, the endometrium tissue directly adjacent the applicator is heated to a temperature in the range of 50° C. to about 90° C., for period of up to 60 minutes. Then the EMR energy is shut off, the applicator is then withdrawn. In practice, it has been found that by utilizing EMR energy at 915 MHz, and with normal blood perfusion, the temperature beyond 1.5 cm is not elevated above 43° C. when the applicator temperatures are raised to 70° C. Above about 41.5° C., mammalian cells in vitro demonstrate a break point above which a doubling of the biological effectiveness in kill cells occurs for every one degree Centigrade increase in temperature. Above about 55–60° C., thermal necrosis begins and between about 70–110° C., instantaneous coagulation necrosis occurs.

From the foregoing, disclosed are methods and apparatus for the thermal therapeutic treatment of body tissues in a nonsurgical manner. In accordance with the equipment of the invention, an applicator employs one or more helical-coil EMR antennas that are insertable with respective conduits of a pliable catheter. One or more temperature sensors of an array are also inserted into a tubular conduit of the catheter to thereby monitor the temperature generated by the EMR energy absorbed in tissues surrounding the applicator. The applicator can be of the type having an expandable portion thereof which, when inflated, causes the EMR antennas as well as the temperature sensor to balloon outwardly and cause conformance of the body cavity being treated. When the EMR antennas are driven with a frequency of 915 MHz, the helical coils generate a light bulb shaped heating pattern which is ideally suited for the light bulb shaped uterine cavity. This nonsurgical treatment is well adapted for the management of menorrhagia to ablate the endometrium tissue lining the inside of the uterine cavity. It can be appreciated that the individual advantages of the various embodiments or structures can be combined to achieve or optimize the performance or efficiency of the invention.

While the preferred and other embodiments of the invention have been disclosed with reference to specific applicators, system equipment, software and programming techniques, it is to be understood that many changes in detail may be made as a matter of engineering choices without departing from the spirit and scope of the invention, a defined by the appended claims.

What is claimed is:

1. A method for thermally treating tissue of a body cavity having an entrance opening and a closed end, and that is irregular shaped when collapsed, comprising the steps of:

inserting a catheter portion of an applicator having an antenna into the entrance opening of the collapsed body cavity;

expanding in the collapsed body cavity a noncompliant angioplasty type balloon to a fixed shape that is different from that of the collapsed body cavity to conform the shape of the body cavity to said fixed shape;

applying electromagnetic energy to the antenna at a power level and for a time interval sufficient to cause ablation of the tissue of the body cavity including the closed end thereof; and producing a transmitted electromagnetic radiation pattern by said antenna, said radiation pattern having a shape generally the same as the fixed shape of the expanded angioplasty type balloon.

2. The method of claim 1 further including conforming a uterine cavity to a pear shape with said angioplasty type balloon, and ablating a desired thickness of the endometrium tissue.

3. The method of claim 1, further including expanding a portion of the applicator so as to force the tissue of the body cavity to conform to said fixed shape.

4. The method of claim 3, further including compressing the body tissue and reducing blood flow therein, thereby reducing thermal dissipation caused by the flow of blood in said tissue.

5. The method of claim 1, further including expanding said balloon catheter so as to change the irregular shape of the collapsed body cavity to a predefined shape defined by said fixed shape.

6. The method of claim 1, further including a plurality of antennas, and positionally inserting said antennas into respective lumens of the catheter portion of the applicator to achieve a desired radiation pattern.

7. The method of claim 1, further including thermally treating body tissues of non-uniform thickness by simultaneously causing a higher density of energy to be induced into the thicker tissue and a lower density of energy to be induced into the thinner tissue.

8. The method of claim 1, further including using an applicator having a spiral antenna curved over a tip thereof so as to provide radiation axially from the tip of said antenna.

9. A method for ablating endometrial tissue of a uterine cavity, comprising the steps of:

inserting a balloon catheter having at least one antenna therein into the uterine cavity; and applying electrical energy to said antenna so as to produce an electromagnetic radiation for treating the endometrial tissue of the uterine cavity, said antenna being configured so that said radiation pattern is generally an inverted pear shape.

10. The method of claim 9, further including expanding an angioplasty type of balloon catheter to enlarge the uterine cavity and move the cornus portions thereof toward each other and closer to said antenna.

11. The method of claim 10, further including moving the cornus portions so that the isotherms more uniformly heat the cornus portions of the uterus.

12. The method of claim 9, further including conforming the physical shape of the antenna to at least a portion of said pear shape.

13. An applicator for generating electromagnetic energy and insertable into a body cavity for treatment of body tissues, comprising:

a catheter having a portion thereof that is expandable when pressure is applied thereto, a body portion of said catheter having at least one lumen constructed therein, said lumen extending into said expandable portion of the catheter; and an antenna supported by the catheter lumen, whereby when said catheter portion is expanded, the tissue of the body cavity and the expandable portion of the catheter are forced to conforming shapes, and the physical shape of the antenna conforms to the shape of the body tissue in contact with the expandable portion of the catheter.

14. The applicator of claim 13, wherein said catheter includes a cavity that can be filled with a fluid so that a pressure thereof causes an expansion of the expandable portion.

15. The applicator of claim 13, wherein the expandable portion of said catheter expands to a predefined shape that is independent of the shape of the body cavity.

16. The applicator of claim 13, further including a plurality of antennas insertable within respective lumens formed in said catheter body.

17. The applicator of claim 13, further including means for circulating a cooling liquid through said applicator.

18. The applicator of claim 13, further including means for mechanically expanding a balloon portion of said catheter.

19. The applicator of claim 13, wherein said antenna comprises a helical coil formed in a curve around a distal tip of said catheter expandable portion.

20. The method of claim 9, further including treating non-uniform thicknesses of uterine cavity tissue by offsetting an axial axis of the antenna with respect to an axis of the balloon.

21. An applicator for generating electromagnetic energy and insertable into a body cavity for treatment of body tissues, comprising:

a catheter having a portion thereof that is expandable to a shaped envelope when pressure is applied thereto, a body portion of said catheter having at least one lumen constructed therein; and an elongate antenna structure supported by the catheter lumen, and being insertable into the catheter lumen so as to be disposed centrally within said envelope when expanded, said antenna producing a radiation pattern generally the same shape as a sidewall and end surface of said envelope when expanded.

22. The method of claim 1, further including expanding the angioplasty type balloon to the fixed shape to thereby open cornus portions of a uterus against an outer surface of said balloon.

* * * * *